United States Patent [19]

Kilgour et al.

[11] Patent Number: 4,526,996

[45] Date of Patent: Jul. 2, 1985

[54] PROCESS FOR THE PREPARATION OF N-SUBSTITUTED AMINOALKYLSILANES

[75] Inventors: John A. Kilgour, Putnam Valley, N.Y.; Herbert E. Petty, Bethel, Conn.

[73] Assignee: Union Carbide Corporation, Danbury, Conn.

[21] Appl. No.: 622,176

[22] Filed: Jun. 19, 1984

[51] Int. Cl.³ ................................................ C07F 7/10
[52] U.S. Cl. .................................... 556/413; 556/424; 544/358; 546/14; 548/110
[58] Field of Search ................ 556/413, 424; 544/358; 546/14; 548/110

[56] References Cited

U.S. PATENT DOCUMENTS

| | | | |
|---|---|---|---|
| 3,033,815 | 5/1962 | Pike et al. | 556/413 X |
| 3,046,295 | 7/1962 | Lisanke et al. | 556/424 |
| 4,045,460 | 8/1977 | Kleinstück | 556/413 |

*Primary Examiner*—Paul F. Shaver
*Attorney, Agent, or Firm*—Paul W. Leuzzi, II

[57] ABSTRACT

N-substituted aminoalkylsilanes are obtained via a selective process which comprises reacting a cyanoalkylsilane with a primary or secondary amine in the presence of a heterogeneous hydrogenation catalyst selected from the group consisting of rhodium, platinum and palladium.

17 Claims, No Drawings

PROCESS FOR THE PREPARATION OF N-SUBSTITUTED AMINOALKYLSILANES

FIELD OF THE INVENTION

This invention relates to a process for the preparation of aminoalkylsilanes. More particularly, this invention relates to the formation of N-substituted aminoalkylsilanes by reacting a cyanoalkylsilane with a primary or secondary amine in the presence of a catalyst.

BACKGROUND OF THE INVENTION

The basic process for producing aminoalkylsilanes is taught in U.S. Pat. No. 3,046,295 to Lisanke, et al., which discloses that cyanoalkylsilanes can be reacted with alkylene amines in the presence of hydrogen and a hydrogenation catalyst, such as Raney Nickel, Girdler nickel or bis(cyclopentadienyl) nickel. However, it has been found that most hydrogenation catalysts yield a high percentage of unsubstituted aminoalkylsilane, i.e. a silane wherein the cyanoalkylsilane is simply reduced to form an unsubstituted primary amine without "coupling" with the amine reactant.

Accordingly, there is a need for a selective process for the preparation of N-substituted aminoalkylsilanes.

SUMMARY OF THE INVENTION

The present invention provides an improved process for preparing an N-substituted aminoalkylsilane by reacting a primary or secondary amine with a cyanoalkylsilane in the presence of hydrogen gas and a heterogeneous hydrogenation catalyst selected from the group consisting essentially of rhodium, platinum and palladium. The process provides greatly increased selectivity to the N-substituted aminoalkylsilane.

DETAILED DESCRIPTION OF THE INVENTION

The primary or secondary amines useful in the present invention contain at least one hydrogen bonded to a nitrogen that will react with the cyano group of the cyanoalkylsilane.

Suitable primary and secondary amines are monoamines, polyamines and heterocyclic amines. The monoamines and the polyamines useful in this invention are represented by the formula:

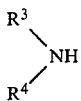

wherein $R^3$ and $R^4$ are individually hydrogen or a substituted or unsubstituted alkyl, aryl or alkyleneamine group containing 1 to 12 carbon atoms preferably an alkyl group containing 1 to 4 carbon atoms. For the avoidance of doubt, $R^3$ and $R^4$ may be the same or different, except that $R^3$ and $R^4$ may not both be hydrogen.

When neither $R^3$ and $R^4$ are alkyleneamine then the amine is a monoamine and when at least one $R^3$ or $R^4$ is an alkyleneamine the amine is a polyamine.

Examples of suitable primary and secondary monoamines include ethylamine, n-propylamine, isopropylamine butylamine, octylamine, dimethylamine, diethylamine, methylethylamine, methyl isopropylamine, dibutylamine, methylbutylamine, ethylbutylamine, dioctylamine, methyloxytylamine, ethyloctylamine, cyclohexylamine, aniline, naphthylamine, benzylamine, and 2-phenylethylamine.

Suitable primary and secondary polyamines include ethylenediamine, 1,3-diaminopropane, 1,4-diaminobutane, 1,6-diaminohexane, 3,4-diaminohexane, 1,4-diamino-2,2-dimethylbutane, N,N'-dimethylethylenediamine, N,N-dimethylethylenediamine, diethylenetriamine, triethylenetetramine, and tetraethylenepentamine.

The heterocyclic amines useful in the present invention are represented by the formula:

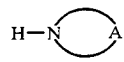

wherein A is a divalent 4, 5, or 6 membered chain wherein the chain members are only carbon or carbon and one member selected from the group of oxygen, sulfur, and an amino moiety.

Examples of suitable heterocyclic amines include piperazine, morpholine, pyrrolidine and piperadine.

Also useful in the present invention are amines of the formula

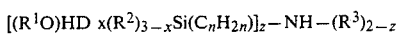

where $R^1$ and $R^2$ are individually substituted or unsubstituted alkyl or aryl groups having from 1 to 12 carbon atoms, preferably alkyl groups having 1 to 4 carbon atoms; x is an integer from 0 to 3; n is an integer from 2 to 4; z is an integer from 1 to 2; and $R^3$ is as set forth above.

Examples of suitable primary and secondary silicon-containing monoamines include
3-aminopropyltriethoxysilane,
3-aminopropyltrimethoxysilane,
2-aminopropylmethyldiethoxysilane, and
3-aminopropyltrimethylsilane. Examples of suitable primary and secondary silicon-containing polyamines include
N-(2-aminoethyl)-3-aminopropyltriethoxysilane and
N-(2-aminoethyl)-3-aminopropyltrimethoxysilane.

These silicon-containing amines can be prepared either as products of the present invention or via conventional routes, such as the condensation of the appropriate amine and a corresponding chloroalkylsilane.

Suitable cyanoalkylsilanes are represented by the formula:

wherein $R^1$, $R^2$, n and x are as previously defined.

Examples of cyanoalkylsilanes that are useful in this invention include 2-cyanoethyltriethoxysilane, 2-cyanoethyltrimethoxysilane, 5-cyanopentyltriethoxysilane, 3-cyano-2,2-dimethylpropylmethyldiethoxysilane, 2-cyanoethylethyldibutoxysilane, 2-cyanoethylmethyldiheptoxysilane, 3-cyano-2-methylpropyltriethoxysilane, 2-cyanoethyl(cyclohexyl)diethoxysilane, 2-cyanoethyltrioctoxysilane, and 2-cyanoethylheptyldiethoxysilane 2-cyanoethylmethyldiethoxysilane, 3-cyanopropylmethyldimethoxysilane, 3-cyanoisobutylphenylethoxymethoxysilane, 2-cyanoethyl(para-n-butylphenyl)diethoxysilane, 2-cyanoethyl(3-phenylpropyl)diethoxysilane, 2-cyanopropylnaphthyldiethoxysilane. These silanes may be prepared in a variety of known ways, such as is disclosed in U.S. Pat. No. 3,046,295.

The ratio of primary or secondary amine to cyanoalkylsilane used in the process of this invention is not critical. However, lower ratios of amine to cyanoalkylsilane lead to lower selectivity for the desired N-substituted aminoalkylsilane as opposed to the simple reduction product from the cyanoalkylsilane reactant. Thus the molar ratio of primary or secondary amine to cyanoalkylsilane would preferably range from 1 to 10, and more preferably from 3 to 10.

Surprisingly it has been found that the choice of hydrogenation catalyst is critical in achieving high selectivity for the desired N-substituted aminoalkylsilane. The nickel catalysts of U.S. Pat. No. 3,046,295 generally yield more unsubstituted (primary) aminoalkylsilane than N-substituted aminoalkylsilane and so have selectivity ratios of N-substituted aminoalkylsilanes to unsubstituted aminoalkylsilanes of less than 1:1. However, it has now been found that the only hydrogenation catalysts which exhibit selectivity ratios of greater than 1:1 for the N-substituted aminoalkylsilanes are heterogeneous catalysts made from rhodium, platinum and palladium. By heterogeneous, what is meant is the powdered metal is present on a catalyst support such as alumina or carbon. However, the form of catalyst support is not critical, both powdered and pelletized forms are considered useful in this invention.

The hydrogen pressure that is maintained during the reaction is not critical and may generally vary from about 50 psig to about 1000 psig. For a rhodium catalyst, the preferred range of hydrogen pressure is from about 400 psig to about 700 psig. For a platinum catalyst, the preferred range of hydrogen pressure is from about 300 psig to about 750 psig. The preferred hydrogen pressure range for a palladium catalyst is about 50 psig to about 750 psig.

The temperature maintained during the reaction is not narrowly critical. Temperatures between about 25° C. and about 180° C. are generally preferred. Lower temperatures may lead to low catalyst activity and higher temperatures may cause undesirable side reactions. The most preferred temperature range for rhodium is from about 100° C. to about 150° C., for platinum from about 130° C. to about 170° C. and for palladium from about 150° C. to about 170° C.

The reaction mixture can contain a solvent in addition to the reactants and catalyst. Suitable solvents include aromatic hydrocarbons, such as toluene, and aliphatic alcohols such as methanol and ethanol. It has also been found that by using a lower alkanol, such as methanol or ethanol, as a solvent, in an amount from about 1% to about 10% by weight of the total reaction solution, the lifetime of a rodium or platinum catalyst can be increased. This is evidenced by increased activity in recycled catalyst from reactions where a lower alkanol solvent was used. However, a lower alkanol solvent appears to suppress the activity of a palladium catalyst. Furthermore, the selection of the alkanol must be compatible with the desired product because transesterification of the alkoxy groups in silane reactants or products may occur under the chosen reaction conditions.

The process of the present invention yields N-substituted aminoalkylsilanes and unsubstituted aminoalkylsilanes. However, unlike the prior processes, the present invention allows for greater N-substituted aminoalkylsilane selectivity, i.e. greater than 1:1 and in instances up to 24:1 or higher. The N-substituted aminoalkylsilane, which is the desired endproduct, is represented by the formula:

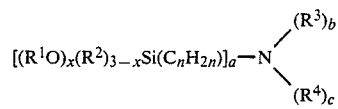

wherein $R^1$, $R^2$, $R^3$, $R^4$, x and n are as defined above and a is an integer of from 1 to 3, b is an integer of from 0 to 2 and c is an integer of from 0 to 2 with the proviso that a+b+c equals 3.

The reaction mechanism which provides this product is believed to be as follows:

I. Primary Amine

II. Silicon-Containing Primary Amine

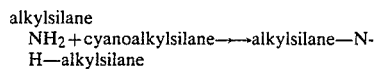

III. Secondary Amine

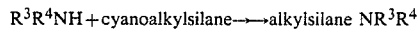

IV. Silicon-Containing Secondary Amine

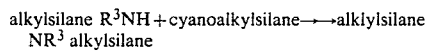

The reaction product a primary amine or silicon-containing primary amine with cyanoalkylsilane can be subsequently reacted with more cyanoalklyamine to replace the free hydrogen with another alkylsilicon group.

The following are illustrative, but not all inclusive, examples of products that can be made with this process:
N-(2'-aminoethyl)-3-aminopropyltriethoxysilane
N-(2'-aminoethyl)-3-aminopropyltrimethoxysilane
N'-(2''-aminoethyl)-N-(2'-aminoethyl)-3-aminopropyltriethoxysilane
N'-(2''-aminoethyl)-N-(2'-aminoethyl)-3-aminopropyltrimethoxysilane
N-butyl-3-aminopropyltriethoxysilane
N-octyl-3-aminopropyltrimethoxysilane
N-cyclohexyl-3-aminopropyltriethoxysilane
N-(3'-triethoxysilylpropyl)-piperazine
N,N'-bis(3'-triethoxysilylpropyl)-piperazine
bis-(3-triethoxysilylpropyl)amine
tris-(3-trimethoxysilylpropyl)amine
bis-N,N'-(3'-triethoxysilylpropyl)ethylenediamine
tris-N,N,N'-(3'-trimethoxysilylpropyl)ethylenediamine
N,N-dimethyl-3-aminopropyltriethoxysilane
N-methyl-N-butyl-3-aminopropyltriethoxysilane
N-(3'-aminopropyl)-3-aminopropyltriethoxysilane
N-(3'-triethoxysilylpropyl)morpholine
N'-(3'-aminopropyl)-5-aminopentyltripropoxysilane
N-(3-triethoxysilylpropyl)-N-5'-triethoxysilylpentyl)amine
N-(3'trimethoxysilylpropyl)-N'-(5''-trimethoxysilylpentyl)piperazine
N-(2'-aminoethyl)-3-aminopropylethyldiethoxysilane
N-(2'-aminoethyl)-3-aminopropyldiethylethoxysilane Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified. Those examples denoted by a letter are comparative examples outside the scope of the present invention and within the teachings of U.S. Pat. No. 3,046,295.

Definitions

In the table below, the following terms, symbols and abbreviations have the following meanings:
g—grams
ml—milliliters
psig—pounds per square inch
°C.—degrees celsius
hr—hours
Cyanoalkylsilanes:
CNE: 2-cyanoethyltriethoxysilane
CNM: 2-cyanoethyltrimethoxysilane
Amines:
EDA: ethylenediamine
DTA: diethylenetriamine
NBA: n-butylamine
PIP: piperazine
APM: 3-aminopropyltrimethoxysilane
APE: 3-aminopropyltriethoxysilane
BMA: bis-(3-trimethoxysilylpropyl)amine
BEA: bis-(3-triethoxysilylpropyl)amine
TMA: tris-(3-trimethoxysilylpropyl)amine
TEA: tris-(3-triethoxysilylpropyl)amine
EEDA: N-(2'-aminoethyl)-3-aminopropyltriethoxysilane
MEDA: N-(2'-aminoethyl)-3-aminopropyltrimethoxysilane
EPIP: N-(3'-triethoxysilylpropyl)piperazine
MPIP: N-(3'-trimethoxysilylpropyl)piperazine
EDTA: N'-(2"-aminoethyl)-N-(2'-aminoethyl)-3-aminopropyltriethoxysilane
MDTA: N'-(2"-aminoethyl)-N-(2'aminoethyl)-3-aminopropyltrimethoxysilane
Catalysts:
Rh-I: 5% rhodium on carbon
Rh-II: 5% rhodium on alumina
Pt-I: 5% platinum on carbon
Pt-II: 1% platinum on carbon
Pt-III: 5% platinum on alumina
Pt-IV: 0.5% platinum on alumina pellets
Pd-I: 5% palladium on carbon
Ni-I: 50% nickel on kieselguhr
Ni-II: 5% nickel on alumina

EXAMPLE 1

Reaction of 2-Cyanoethyltriethoxysilane with Ethylenediamine and Hydrogen using Rhodium on Carbon Catalyst A one liter autoclave was charged with 150.73 grams (0.695 moles) of 2-cyanoethyltriethoxysilane, 205.09 grams (3.418 moles) of ethylenediamine and 2.85 grams of 5% rhodium on carbon. The autoclave was sealed and purged with hydrogen. The autoclave was pressurized to 575 psi with hydrogen and stirring initiated. The reaction was heated to 132° C. for 16 hours and then cooled. The pressure was released and the product analyzed as 77.5% recovery of ethylenediamine, 0.0% recovered 2-cyanoethytriethoxysilane, 13.8% yield of 3-aminipropyltriethoxysilane, and 60.9% yield of N-(2'-aminoethyl)-3-aminopropyltriethoxysilane.

EXAMPLE 2

Reaction of 2-Cyanoethyltriethoxysilane with n-Butylamine and Hydrogen using Rhodium on Carbon as Catalyst A mixture of 21.7 grams of 2-cyanoethyltriethoxysilane, 8.9 grams of n-butylamine, 50 ml of ethanol, and 2.0 grams of 5% rhodium on carbon was sealed in a 300 cc bomb. The bomb was pressurized to 400 psi at 23° C. After 5.5 hours the bomb was repressurized to 400 psi, and the reaction was continued for 16.5 hours. The product contained a 40/60 mixture of 3-aminopropyltriethoxysilane to N-butyl-3-aminopropyltriethoxysilane.

EXAMPLE 3

Reaction of 2-Cyanoethyltriethoxysilane with Ethylenediamine and Hydrogen using Rhodium and Alumina as Catalyst A mixture of 36.75 grams (0.169 moles) of 2-cyanoethyltriethoxysilane, 35.16 grams (0.586 moles) of ethylenediamine, and 1.0 gram of 5% rhodium on alumina was sealed in a 300 cc bomb. The bomb was sealed and purged with hydrogen. The bomb was pressurized to 600 psi with hydrogen and heated to 150° C. After rocking for twelve hours the bomb was cooled and the products analyzed. In addition to recovery of 30% of the starting ethylenediamine and 0.0% recovery of 2-cyanoethyltriethoxysilane, a 25.7% yield of 3-aminopropyltriethoxysilane and 40.9% yield of N-(2'-aminoethyl)-3-aminopropyltriethoxysilane was observed.

EXAMPLE 4

Reaction of 2-Cyanoethyltriethoxysilane with Piperazine and Hydrogen using Rhodium on Carbon as Catalyst A mixture of 100 grams (0.46 moles) of 2-cyanoethyltriethoxysilane, 140 grams (1.63 moles) of piperazine, and 2.0 grams of 5% rhodium on carbon was sealed in a one liter autoclave. The autoclave was purged with hydrogen and pressurized to 600 psi. The autoclave was heated to 155° C. and stirred for 19 hours. After cooling the product was analyzed as 24.7% 3-aminopropyltriethoxysilane and 55.8% N-(3'-triethoxysilylpropyl)-piperazine.

EXAMPLE 5

Reaction of 2-Cyanoethyltriethoxysilane with Ethylenediamine and Hydrogen using Platinum on Carbon as Catalyst A mixture of 50.86 grams (0.234 moles) of 2-cyanoethyltriethoxysilane, 50.11 grams (0.835 moles) of ethylenediamine and 1.0 gram of 5% platinum on carbon was sealed in a 300 cc bomb. The bomb was purged with hydrogen and pressurized to 600 psi with hydrogen. The bomb was heated to 150° C. for 26 hours while rocking. After cooling the product solution was analyzed as containing 80.4% recovered ethylenediamine, 32.9% recovered 2-cyanoethyltriethoxysilane, a trace of 3-aminopropyltriethoxysilane, and 62.8% N-(2'-aminoethyl)-3-aminopropyltriethoxysilane.

EXAMPLE 6

Reaction of 2-Cyanoethyltriethoxysilane with Piperazine and Hydrogen using Platinum on Carbon as Catalyst A mixture of 200.73 grams (0.925 moles) of 2-cyanoethyltriethoxysilane, 249.58 grams (2.90 moles) of piperazine and 5 grams of 5% platinum on carbon was placed in a one liter stirred autoclave. The autoclave was purged with hydrogen and pressurized to 750 psi with hydrogen. The autoclave was stirred and heated to 150° for 19 hours. After cooling the product solution was analyzed to show a 6.3% yield of 3-aminopropyltriethoxysilane and 67.2% yield of N-(3'-triethoxysilylpropyl)-piperazine.

EXAMPLE 7

Reaction of 2-Cyanoethyltrimethoxysilane with Ethylenediamine and Hydrogen using Platinum on Carbon as Catalyst and Methanol Solvent A mixture of 40.0 grams of 2-cyanoethyltrimethoxysilane, 50.0 grams of ethylenediamine, 10.0 grams of methanol and 2.0 grams of 1% platinum on carbon was sealed in a 300 cc bomb. The bomb was purged with hydrogen and pressurized to 750 psi. The bomb was heated to 150° C. and rocked for 21 hours. After cooling the product was analyzed as 3.3% yield of 3-aminopropyltrimethoxysilane and 80.4% yield of N-(2'-aminoethyl)-3-aminopropyltrimethoxysilane.

EXAMPLE 8

Reaction of 2-Cyanoethyltrimethoxysilane with Ethylenediamine and Hydrogen using Platinum on Alumina as Catalyst A mixture of 200.2 grams (1.14 moles) of 2-cyanoethyltrimethoxysilane, 275 grams (4.58 moles) of ethylenediamine, and 10 grams of 5% platinum on alumina was sealed in a one liter autoclave. The autoclave was purged with hydrogen and pressurized to 750 psi with hydrogen. The autoclave was heated to 150° C. and stirred for 19 hours. After cooling the product was analyzed as 7.9% yield of 3-aminopropyltrimethoxysilane and 77.8% yield of N-(2'-aminoethyl)-3-aminopropyltrimethoxysilane.

EXAMPLE 9

Reaction of 2-Cyanoethyltrimethoxysilane with Diethylenetriamine and Hydrogen using Platinum on Alumina Catalyst A mixture of 200.41 grams (1.15 moles) of 2-cyanoethyltrimethoxysilane, 357.20 grams (3.47 moles) of diethylenetriamine, and 8 grams of 5% platinum on alumina was sealed in a one liter autoclave. The autoclave was heated to 150° C. and stirred for 19 hours. After cooling the product was analyzed as 12.3% yield of 3-aminopropyltriethoxysilane and 83.3% yield of N'-(2'-aminoethyl)-N-(2'aminoethyl)-3-aminopropyltrimethoxysilane.

EXAMPLE 10

Reaction of 2-Cyanoethyltriethoxysilane with Ethylenediamine and Hydrogen using Platinum on Alumina as Catalyst A mixture of 50.0 grams of 2-cyanoethyltriethoxysilane, 50 grams of ethylenediamine and 2.50 grams of 5% platinum on alumina was sealed in a 300 cc bomb. The bomb was purged with hydrogen, pressurized to 750 psi with hydrogen, heated to 150° C. and rocked for 21 hours. After cooling the reaction was analyzed as 7.7% yield of 3-aminopropyltriethoxysilane and 87.8% yield of N-(2'-aminoethyl)-3-aminopropyltriethoxysilane.

EXAMPLE 11

Reaction of 2-Cyanoethyltrimethoxysilane with Diethylenetriamine and Hydrogen using Platinum on Alumina A mixture of 200.41 grams (1.15 moles) of 2-cyanoethyltrimethoxysilane, 357.20 grams (3.47 moles) of diethylenetriamine, and 8.0 grams of 5% platinum on alumina was sealed in a one liter autoclave. The autoclave was purged with hydrogen and pressurized to 750 psi with hydrogen. The autoclave was heated to 150° C. and stirred for 19 hours. After cooling the product was analyzed to show 10.4% yield of 3-aminopropyltrimethoxysilane and 70.8% yield of N'-(2'-aminoethyl)-N-(2'-aminoethyl)-3-aminopropyltrimethoxysilane.

EXAMPLE 12

Reaction of 2-Cyanoethyltriethoxysilane with a 1 to 9.8 mixture of 3-Aminopropyltriethoxysilane to N-(2'-Aminoethyl)-3-aminopropyltriethoxysilane and Hydrogen using Platinum on Alumina Catalyst A mixture of 201 grams (0.926 moles) of 2-cyanoethyltriethoxysilane, 250 grams of a 1 to 9.8 molar mixture of 3-aminopropyltriethoxysilane to N-(2'-aminoethyl)-3-aminopropyltriethoxysilane, and 8 grams of 5% platinum on alumina were sealed in a one liter autoclave. The autoclave was purged with hydrogen and pressurized to 750 psi with hydrogen. The autoclave was heated to 150° C. for 19 hours. After cooling the product was analyzed as 10.9% yield of 3-aminopropyltriethoxysilane, 6.3% yield of N-(2'-aminoethyl)-3-aminopropyltriethoxysilane, 22.2% yield of bis-3-triethoxysilylpropylamine, 7.7% yield of bis-1.3-(3-aminopropyl) 1,1,3,3-tetramethoxydisiloxane, 41.2% yield of bis-N,N'-(3-triethoxysilylpropyl)-ethylenediamine, and 6.8% yield of tris-N,N,N'-(3-triethoxysilylpropyl)ethylenediamine.

EXAMPLE 13

Reaction of 2-Cyanoethyltrimethoxysilane with a 9.7 to 1 Molar Mixture of N-(2'-Aminoethyl)-3-aminopropyltrimethoxysilane to 3-Aminopropyltrimethoxysilane and Hydrogen with Platinum on Alumina Catalyst A mixture of 166.25 grams (0.95 moles) of 3-aminopropyltrimethoxysilane, 199.5 grams of 9.7 to 1 molar mixture of N-(2'-aminoethyl)-3-aminopropyltrimethoxysilane to 3-aminopropyltrimethoxysilane, and 8.3 grams of 5% platinum on alumina was sealed in a one liter autoclave. The autoclave was heated to 150° C. for 19 hours. After cooling was analyzed 26.5% yield of 3-aminopropyltrimethoxysilane, 27.5% yield of N-(2'-aminoethyl)-3-aminopropyltrimethoxysilane, 7.4% yield of bis-3-trimethoxysilylpropylamine, and 26.3% yield of bis-N,N'-(3-trimethoxysilylpropyl)ethylenediamine.

EXAMPLE 14

Reaction of 2-Cyanoethyltriethoxysilane with Diethylenetriamine and Hydrogen using Platinum on Alumina Pellets as Catalyst A mixture of 50.88 grams (0.234 moles) of 2-cyanoethyltriethoxysilane, 74.19 grams (0.720 moles) of diethylenetriamine, and 20 grams of 0.5% platinum on alumina pellets was sealed in a 300 cc bomb. The bomb was purged with hydrogen and pressurized to 750 psi with hydrogen. The bomb was heated to 150° C. and rocked for 16 hours. After cooling the product was analyzed as 6.4% yield of 3-aminopropyltriethoxysilane and 76.9% yield of N'-(2''-aminoethyl)-N-(2'-aminoethyl)-3-aminopropyltriethoxysilane.

EXAMPLE 15

Reaction of 2-Cyanoethyltriethoxysilane with Ethylenediamine and Hydrogen using Palladium on Carbon as Catalyst A mixture of 50 grams (0.230 moles) of 2-cyanoethyltriethoxysilane, 50 grams (0.819 moles) of ethylenediamine, and 3.0 grams of 5% palladium on carbon was sealed in a 300 cc bomb. The bomb was purged with hydrogen and pressurized to 750 psi with hydrogen. The bomb was heated to 160° C. and rocked for twenty hours. After cooling, the product was analyzed as 0.6% 3-aminopropyltriethoxysilane and 41.0% N-(2'-aminoethyl)-3-aminopropyltriethoxysilane.

EXAMPLE 16

Reaction of 2-Cyanoethyltriethoxysilane with Ethylenediamine and Hydrogen using Platinum on Alumina Catalyst and Methanol Cosolvent A mixture of 35.0 grams of 2-cyanoethyltriethoxysilane, 35.0 grams of ethylenediamine, 70.0 grams of methanol, and 1.75 grams of 5% platinum on alumina was sealed in a 300 cc bomb. The bomb was purged with hydrogen, pressurized to 750 psi with hydrogen, heated to 150° C. and rocked for 16 hours. After cooling the product was analyzed as 3.6% yield of 3-aminopropyltrialkoxysilane and 89.1% yield of N-(2'-aminoethyl)-3-aminopropyltrialkoxysilanes.

EXAMPLE 17

Reaction of 2-Cyanoethyltriethoxysilane with Ethylenediamine and Hydrogen using Rhodium on Carbon Catalyst and Toluene Solvent A mixture of 21.7 grams of 2-cyanoethyltriethoxysilane, 12.0 grams of ethylenediamine, 33.7 grams of toluene, and 2.0 grams of 5% rhodium on carbon was sealed in a 300 cc bomb. The bomb was pressurized to 405 psi and heated to 60° C. The reaction was rocked for 17.25 hours. After cooling the product was analyzed as 30.6% 3-aminopropyltriethoxysilane and 59.4% N-(2'-aminoethyl)-3-aminopropyltriethoxysilane.

EXAMPLE 18

Recycling Platinum on Alumina Catalyst in Reactions of 2-Cyanoethyltriethoxysilane with Ethylenediamine and Hydrogen A mixture of 50.0 grams (0.230 moles) of 2-cyanoethyltriethoxysilane, 50.0 grams (0.819 moles) of ethylenediamine, and 2.50 grams of 5% platinum on alumina was sealed in a 300 cc bomb. The bomb was purged with hydrogen and pressurized to 750 psi. The bomb was heated to 150° C. for 21 hours and rocked. After cooling the catalyst was isolated by filtration, washed with methanol under nitrogen and vacuum dried. The reaction was then repeated using the recovered catalyst. Upon completion of the second reaction, a third cycle was run using the same procedure. Catalyst activity was indicated by following hydrogen up take. In the first cycle the initial rate of hydrogen uptake was 5.0 m moles of hydrogen/min. In the third cycle the initial rate of hydrogen uptake was 0.3 m moles of hydrogen/min.

EXAMPLE 19

Recycling the Platinum on Alumina Catalyst in Reactions of 2-Cyanoethyltriethoxysilane with Ethylenediamine and Hydrogen using Methanol as a Catalyst A mixture of 35.0 grams (0.161 moles) of 2-cyanoethyltriethoxysilane, 35.0 grams (0.573 moles) of ethylenediamine, 70.0 grams of methanol, and 1.75 grams of 5% platinum on alumina were sealed in a 300 cc bomb. The bomb was purged with hydrogen, pressurized to 750 psi and was heated to 150° C. for 16 hours. The catalyst was separated by filtration, washed with methanol and vacuum dried for one hour. The reaction was repeated a second time using catalyst from the first reaction. A third reaction was similarly run using catalyst isolated from the second reaction. The catalyst activity was indicated by the rate of hydrogen uptake. For the three cycles the rates were $1.45 \times 10^{-3}$ moles/min, $0.95 \times 10^{-3}$ moles/min and $0.83 \times 10^{-3}$ moles/min.

EXAMPLE A

A mixture of 127.2 grams (0.586 moles) of 2-cyanoethyltriethoxysilane, 174.8 grams (2.91 moles) of ethylenediamine, and 0.50 grams of 50% nickel on kieselguhr was sealed in a one liter autoclave. The autoclave was purged with hydrogen and pressurized to 650 psi with hydrogen. The autoclave was heated to 150° C. and stirred for 18.5 hours. After cooling, the product was analyzed as 70.44% 3-aminopropyltriethoxysilane, and 28.76% N-(2'-aminoethyl)-3-aminopropyltriethoxysilane.

EXAMPLE B

A mixture of 50.0 grams (0.23 moles) of 2-cyanoethyltriethoxysilane, 50.0 grams (0.83 moles) of ethylenediamine, and 0.80 grams of 50% nickel on kieselguhr was sealed in a 300 cc bomb. The bomb was purged with hydrogen and pressurized to 250 psi with hydrogen. The bomb was heated to 160° C. and rocked for 16 hours. After cooling the product was analyzed as 69.38% 3-aminopropyltriethoxysilane, and 25.77% N-(2'-aminoethyl)-3-aminopropyltriethoxysilane.

EXAMPLE C

A mixture of 50.0 grams (0.23 moles) of 2-cyanoethyltriethoxysilane, 75 grams (0.73 moles) of diethylenetriamine, and 0.625 grams of 50% nickel on kieselguhr was sealed in a 300 cc bomb. The bomb was purged with hydrogen and pressurized to 500 psi with hydrogen. The bomb was heated to 150° C. and rocked for 13 hours. After cooling, the product was analyzed as 83.71% 3-aminopropyltriethoxysilane, and 16.29% of N'-(2-aminoethyl)-N-(2'-aminoethyl)-3-aminopropyltriethoxysilane.

EXAMPLE D

A mixture of 50.0 grams (0.23 moles) of 2-cyanoethyltriethoxysilane, 75 grams (0.73 moles) of diethylenetriamine, and 0.5 grams of 50% nickel on kieselguhr was sealed in a 300 cc bomb. The bomb was purged with hydrogen and pressurized to 700 psi with hydrogen. The bomb was heated to 150° C. and rocked for 15.8 hours. After cooling the product was analyzed as 70.78% 3-aminopropyltriethoxysilane, and 29.22% N'-(2-aminoethyl)-N-(2'-aminoethyl)-3-aminopropyltriethoxysilane.

EXAMPLE E

A mixture of 127.2 grams (0.586 moles) of 2-cyanoethyltriethoxysilane, 175.6 grams (2.93 moles) of ethylenediamine, and 5.0 grams of 5% nickel on alumina was sealed in a one liter autoclave. The autoclave was purged with hydrogen and pressurized to 800 psi with hydrogen. The autoclave was heated to 150° C. and stirred for 19 hours. After cooling, the product was analyzed as N-(2'-aminoethyl)-3-aminopropyltriethoxysilane.

The following tables summarized the results of the foregoing examples, wherein the symbols, terms and abbreviations have the meanings indicated above.

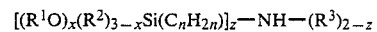

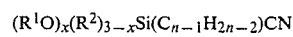

wherein $R^1$ and $R^2$ are individually substituted or unsubstituted alkyl or aryl groups having from 1 to 12 carbon atoms; $R^3$ and $R^4$ are individually hydrogen or a substituted or unsubstituted alkyl, aryl or alkyleneamine group containing 1 to 12 carbon atoms; A is a divalent 4, 5, or 6 membered chain wherein the chain members are only carbon or carbon and one member selected from the group or oxygen, sulfur, and an amino moiety; x is an integer from 0 to 3; n is an integer from 2 to 4; and z is an integer from 1 to 2.

3. The process of claim 1 wherein the cyanoalkylsilane is of the formula:

$$(R^1O)_x(R^2)_{3-x}Si(C_{n-1}H_{2n-2})CN$$

TABLE 1

| Example: | 1 | 2 | 3 | 4 | 5 | 6 | 7 | 8 |
|---|---|---|---|---|---|---|---|---|
| Cyanoalkylsilane; (g) | CNE; 150.73 | CNE; 21.7 | CNE; 36.75 | CNE; 100 | CNE; 50.86 | CNE; 200.73 | CNM; 40.0 | CNM; 200.2 |
| Amine Reactant; (g) | EDA: 205.09 | NBA; 8.9 | EDA; 35.16 | PIP; 140 | EDA; 50.11 | PIP; 249.58 | EDA; 50.0 | EDA; 275 |
| Catalyst; (g) | Rh-I; 2.85 | Rh-I; 2.0 | Rh-II; 1.0 | Rh-I; 2.0 | Pt-I; 1.0 | Pt-I; 5.0 | Pt-II; 2.0 | Pt-III; 10 |
| Solvent (ml) | None | ethanol; 50 | None | None | None | None | methanol, 10 | None |
| H2 Pressure (psig) | 575 | 400 | 600 | 600 | 600 | 750 | 750 | 750 |
| Temp. (°C.) | 132 | 23 | 150 | 155 | 150 | 150 | 150 | 150 |
| Time (hr) | 16 | 16.5 | 12 | 19 | 26 | 19 | 21 | 19 |
| Selectivity | 4.4 | 1.5 | 1.6 | 2.3 | 00 | 10.7 | 24.4 | 9.8 |

| Example | 9 | 10 | 11 | 12 | 13 | | 14 | 15 |
|---|---|---|---|---|---|---|---|---|
| Cyanoalkylsilane; (g) | CNM; 200.41 | CNE; 50.0 | CNM; 200.41 | CNE; 201 | CNM; 166.25 | | CNE, 50.88 | CNE; 50 |
| Amine Reactant; (g) | DTA; 357.20 | EDA; 50 | DTA; 357.20 | APE/EEDA; 250 | ADM/MEDA; 199.5 | | DTA; 74.19 | EDA; 50 |
| Catalyst; (g) | Pt-III; 8 | Pt-III; 2.5 | Pt-III; 8.0 | Pt-III; 8 | Pt-III; 8.3 | | Pt-IV; 20 | Pd-I; 3.0 |
| Solvent (ml) | None | None | None | None | None | | None | None |
| H2 Pressure (psig) | 750 | 750 | 750 | 750 | 750 | | 750 | 750 |
| Temp. (°C.) | 150 | 150 | 150 | 150 | 150 | | 150 | 160 |
| Time (hr) | 19 | 21 | 19 | 19 | 19 | | 16 | 20 |
| Selectivity | 6.8 | 11.4 | 6.8 | >1 | >1 | | 12.0 | 68.3 |

| Example | 16 | 17 | 18 | 19 | A | B | C | D | E |
|---|---|---|---|---|---|---|---|---|---|
| Cyanoalkylsilane; (g) | CNE; 35.0 | CNE; 21.7 | CNE; 50.0 | CNE; 35.0 | CNE; 127.2 | CNE; 50.0 | CNE 41.7 | CNE; 25.9 | CNE; 127.1 |
| Amine Reactant; (g) | EDA; 35.0 | EDA; 12.0 | EDA; 50.0 | EDA; 35.0 | EDA; 174.8 | EDA; 50.0 | DTA; 60.4 | DTA; 77.0 | EDA; 175.6 |
| Catalyst; (g) | Pt-III; 1.75 | Rh-I; 2.0 | Pt-III; 2.50 | Pt-III; 1.75 | Ni-I; 2.1 | Ni-I; 0.8 | Ni-I; 0.5 | Ni-I; 0.25 | Ni-II; 5.0 |
| Solvent (ml) | methanol; 70 | toluene; 33.7 | None | methanol; 70 | None | None | None | None | None |
| H2 Pressure (psig) | 750 | 405 | 750 | 750 | 650 | 250 | 500 | 700 | 800 |
| Temp. (°C.) | 150 | 60 | 150 | 150 | 150 | 160 | 150 | 150 | 150 |
| Time (hr) | 16 | 17.25 | 21 | 16 | 18.5 | 16 | 13 | 15.8 | 19 |
| Selectivity | 24.8 | 1.98 | N/A | N/A | 0.41 | 0.37 | 0.19 | 0.41 | 0.37 |

What is claimed is:

1. A process for selectively preparing an N-substituted aminoalkylsilane which comprises reacting a primary or secondary amine with a cyanoalkylsilane in the presence of hydrogen gas and a heterogeneous hydrogenation catalyst selected from the group consisting of rhodium, platinum and palladium.

2. The process of claim 1 wherein the primary or secondary amine is selected from the group of amines having the structural formula:

wherein $R^1$, $R^2$, n and x are as defined in claim 2.

4. The process of claim 1 wherein the ratio of primary or secondary amine to cyanoalkylsilane is 1 to 10.

5. The process of claim 1 wherein the hydrogen pressure is from 50 psig to 1000 psig.

6. The process of claim 1 wherein the reaction temperature is 25° to 180° C.

7. The process of claim 1 wherein the catalyst is rhodium.

8. The process of claim 1 wherein the catalyst is platinum.

9. The process of claim 1 wherein the catalyst is palladium.

10. The process of claim 1 wherein the reaction takes place in a solvent.

11. The process of claim 10 wherein the solvent is an aromatic hydrocarbon or aliphatical alcohol.

12. The process of claim 11 wherein the aliphatic alcohol is methanol or ethanol.

13. A process for selectively preparing an N-substituted aminoalkylsilane of the formula:

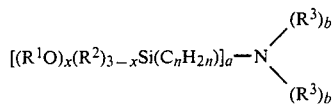

which process comprises reacting a primary or secondary amine selected from the group of amines consisting of:

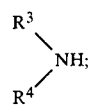

HN A; and

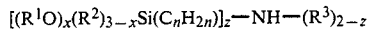

with a cyanoalkylsilane of the formula:

$$(R^1O)_x(R^2)_{3-x}Si(C_{n-1}H_{2n-2})CN$$

wherein $R^1$ and $R^2$ are individually substituted or unsubstituted alkyl or aryl groups having from 1 to 12 carbon atoms; $R^3$ and $R^4$ are individually hydrogen or a substituted or unsubstituted alkyl, aryl or alkyleneamine group containing 1 to 12 carbon atoms; A is a divalent 4, 5, or 6 membered chain wherein the chain members are only carbon or carbon and one member selected from the group of oxygen, sulfur, and an amino moiety; x is an integer from 0 to 3; n is an integer from 2 to 4; and z is an integer from 1 to 2; at 25° to 180° C. in the presence of hydrogen gas, said hydrogen gas having a pressure of from 50 psig to 1000 psig, and in the presence of a heterogeneous hydrogenation catalyst selected from the group consisting of rhodium, platinum and palladium, where the ratio of primary or secondary amine to cyanoalkylsilane is 1 to 10 and where the reaction occurs in an aromatic hydrocarbon or aliphatic alcohol solvent.

14. The process of claim 13 wherein the solvent is methanol or ethanol.

15. The process of claim 13 wherein the catalyst is rhodium, the temperature is from 100° to 150° C. and the hydrogen pressure is from 400 to 700 psig.

16. The process of claim 13 wherein the catalyst is platinum, the temperature is from 130° to 170° C. and the hydrogen pressure is from 300 to 750 psig.

17. The process of claim 13 wherein the catalyst is palladium, the temperature is from 150° to 170° C., the hydrogen pressure is 50 to 750 psig and in the absence of an alkanal solvent.

* * * * *

UNITED STATES PATENT AND TRADEMARK OFFICE
CERTIFICATE OF CORRECTION

PATENT NO. : 4,526,996
DATED : July 2, 1985
INVENTOR(S) : John Alfred Kilgour

It is certified that error appears in the above-identified patent and that said Letters Patent is hereby corrected as shown below:

Claims 2 and 13, formula II of each claim, please delete "HN A" and insert therefor -- HN◯A --.

[SEAL]

Signed and Sealed this

Nineteenth Day of November 1985

Attest:

Attesting Officer

DONALD J. QUIGG

Commissioner of Patents and Trademarks